US012533259B1

United States Patent

Chen et al.

(10) Patent No.: US 12,533,259 B1
(45) Date of Patent: Jan. 27, 2026

(54) METHODS FOR IMPLANTING CORNEAL INLAYS BASED ON HIGH-PRECISION VISUAL AXIS POSITIONING AND INTRAOCULAR PRESSURE ADJUSTMENT

(71) Applicant: EYE HOSPITAL, WENZHOU MEDICAL UNIVERSITY, Zhejiang (CN)

(72) Inventors: Wei Chen, Wenzhou (CN); Mimi Liu, Qionghai (CN); Zihao Liu, Wenzhou (CN); Saiqing Li, Wenzhou (CN)

(73) Assignee: EYE HOSPITAL, WENZHOU MEDICAL UNIVERSITY, Wenzhou (CN)

( * ) Notice: Subject to any disclaimer, the term of this patent is extended or adjusted under 35 U.S.C. 154(b) by 0 days.

(21) Appl. No.: 19/228,836

(22) Filed: Jun. 5, 2025

(51) Int. Cl.
*A61F 9/008* (2006.01)
*A61F 9/007* (2006.01)

(52) U.S. Cl.
CPC ...... *A61F 9/00812* (2013.01); *A61F 9/00781* (2013.01)

(58) Field of Classification Search
CPC .............. A61F 9/00812; A61F 9/00781; A61F 2/1451; A61F 2/148; A61F 9/0084; A61F 9/00836; A61F 9/00834; A61N 5/062; A61L 27/3604; A61L 27/3666
See application file for complete search history.

(56) References Cited

U.S. PATENT DOCUMENTS 6,186,974 B1 * 2/2001 Allan .................. A61F 9/00781 604/30
9,937,033 B1 * 4/2018 Peyman .................. A61L 27/34
10,195,081 B1 * 2/2019 Peyman .............. A61F 9/00736
10,278,920 B1 * 5/2019 Peyman ............... A61K 9/0051
10,952,897 B1 * 3/2021 Smith ................. A61F 9/00825
2002/0161437 A1 * 10/2002 Zhou ......................... A61F 2/16 623/905
2003/0014021 A1 * 1/2003 Holmen ............... A61K 9/0048 604/521
2006/0064077 A1 * 3/2006 Peyman ............. A61F 9/00827 606/5
2008/0228127 A1 * 9/2008 Burns ..................... A61P 27/06 604/9
2018/0344450 A1 * 12/2018 Barker .................... A61F 2/147
2019/0000673 A1 * 1/2019 Fjield .................. A61F 9/00781
2019/0247227 A1 * 8/2019 Peyman ................. A61K 45/06
2020/0289534 A1 * 9/2020 Peyman ............. A61K 31/7064
2022/0409361 A1 * 12/2022 Peyman .............. A61L 27/3604
2023/0404805 A1 * 12/2023 Peyman .................. A61F 2/148

* cited by examiner

*Primary Examiner* — Shirley X Jian
(74) *Attorney, Agent, or Firm* — PORUS IP LLC

(57) ABSTRACT

The present disclosure relates to a method for implanting a corneal inlay based on high-precision visual axis positioning and intraocular pressure adjustment, the method including: performing visual axis positioning on a target object to determine a visual axis center of the target object; producing a corneal implant cavity for the target object; adjusting an intraocular pressure of the target object; and implanting a lens into the corneal implant cavity of the target object to align the lens with the visual axis center of the target object.

16 Claims, 8 Drawing Sheets

Process 100

METHODS FOR IMPLANTING CORNEAL INLAYS BASED ON HIGH-PRECISION VISUAL AXIS POSITIONING AND INTRAOCULAR PRESSURE ADJUSTMENT

TECHNICAL FIELD

The present disclosure relates to the technical field of lens implantation, and in particular to a method for implanting a corneal inlay based on high-precision visual axis positioning and intraocular pressure adjustment.

BACKGROUND

With advances in ophthalmic refractive correction techniques, corneal interlaminar implantation has emerged as an effective approach for correcting refractive errors including presbyopia and hyperopia. Although femtosecond laser-assisted creation of corneal stromal pockets and artificial lens implantation have improved surgical precision, the three-dimensional positioning of lenses still relies heavily on the surgeon's experience, often resulting in postoperative optical center deviation. Most critically, current surgical procedures face a major technical challenge: how to achieve precise manipulation of implanted lenses within the corneal interlaminar tunnel while ensuring rapid and accurate alignment with the patient's visual axis. These issues not only significantly compromise surgical efficiency and unnecessarily prolong procedure duration, but may also increase risks of corneal tissue edema, mechanical damage, and postoperative infection. Furthermore, these issues can lead to complications such as abnormal intraoperative intraocular pressure fluctuations and reduced stability of the corneal interlaminar interface, ultimately posing significant challenges to achieving optimal visual outcomes for patients.

Furthermore, advancements in material science and minimally invasive surgical techniques have driven lens design toward ultra-thin and highly flexible configurations, aiming to minimize interference with corneal biomechanics and improve patient comfort. However, while the substantial reduction in lens thickness enhances tissue compatibility, it also introduces significant challenges in maintaining mechanical stability. During implantation, ultra-thin lenses are susceptible to unintended curling due to external forces, leading to two critical issues. First, real-time intraoperative adjustments become more difficult. The increased friction coefficient between a curled lens and the interlaminar tissue necessitates repeated manipulations for precise repositioning, prolonging surgical duration and elevating the risk of corneal stromal trauma. Second, long-term postoperative stability may be compromised. Lens curling during surgery can exacerbate eccentric displacement, resulting in elevated higher-order aberrations that directly impair visual quality.

Therefore, a method for implanting a corneal inlay based on high-precision visual axis positioning and intraocular pressure adjustment is provided to achieve more precise implant center positioning with more efficient surgical operation, thereby obtaining an ideal optical position of the lens in the corneal lamellae and to complete a high-precision corrective surgery in a minimum period of time, reducing the trauma to the corneal lamellae of the patient, and improving postoperative visual quality and long-term refractive stability of the patient.

SUMMARY

One or more embodiments of the present disclosure provide a method for implanting a corneal inlay based on high-precision visual axis positioning and intraocular pressure adjustment, comprising: performing visual axis positioning on a target object to determine a visual axis center of the target object; producing a corneal implant cavity for the target object; adjusting an intraocular pressure of the target object; and implanting a lens into the corneal implant cavity of the target object to align the lens with the visual axis center of the target object.

BRIEF DESCRIPTION OF THE DRAWINGS

The present disclosure will be further illustrated by way of exemplary embodiments, which will be described in detail by means of the accompanying drawings. These embodiments are not limiting, and in these embodiments, the same numbering denotes the same structure, wherein.

DETAILED DESCRIPTION

Figure 1:
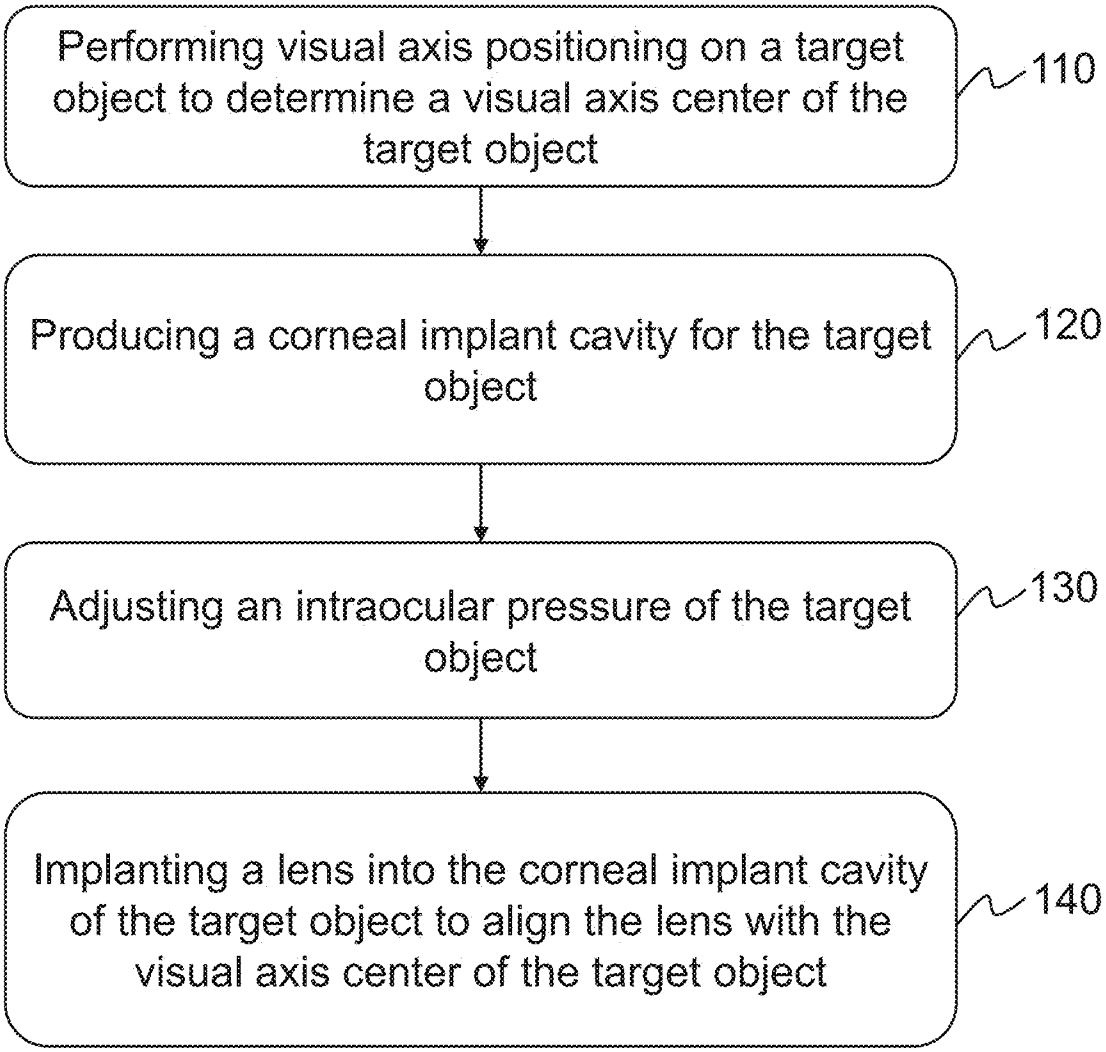
FIG. 1 is a flowchart illustrating an exemplary process for implanting a corneal inlay according to some embodiments of the present disclosure.

In order to more clearly illustrate the technical solutions of the embodiments of the present disclosure, the accompanying drawings required to be used in the description of the embodiments are briefly described below. Obviously, the accompanying drawings in the following description are only some examples or embodiments of the present disclosure, and it is possible for a person of ordinary skill in the art to apply the present disclosure to other similar scenarios in accordance with these drawings without creative labor. The present disclosure can be applied to other similar scenarios based on these drawings without creative labor. Unless obviously acquired from the context or the context illustrates otherwise, the same numeral in the drawings refers to the same structure or operation.

As shown in the present disclosure, unless the context clearly suggests an exception, the words "one", "a", and/or "the" do not refer specifically to the singular, but may also include the plural. Generally, the terms "including" and "comprising" suggest only the inclusion of clearly identified steps and elements. In general, the terms "includes" and "comprises" only suggest the inclusion of explicitly identified steps and elements that do not constitute an exclusive list, and the method may also include other steps or elements.

Some embodiments of the present disclosure provide a method for implanting a corneal inlay. In some embodiments, the method for implanting the corneal inlay includes: performing visual axis positioning on a target object to determine a visual axis center of the target object; producing a corneal implant cavity for the target object; adjusting an intraocular pressure of the target object; and implanting a lens into the corneal implant cavity of the target object to align the lens with the visual axis center of the target object.

In some embodiments, implanting the lens into the corneal implant cavity of the target object is performed via an implantation instrument. More descriptions regarding the implantation instrument may be found in FIG. 4-FIG. 8 and related descriptions.

FIG. 1 is a flowchart illustrating an exemplary process for implanting a corneal inlay according to some embodiments of the present disclosure. The process 100 is an exemplary process of implanting a corneal inlay. As shown in FIG. 1, the process 100 includes the following operations.

In 110, visual axis positioning is performed on a target object to determine a visual axis center of the target object.

The target object refers to an object requiring a surgery of implanting the corneal inlay, for example, a patient with a vision problem. The visual axis positioning refers to positioning the visual axis center of the target object.

In some embodiments, performing the visual axis positioning on the target object to determine the visual axis center of the target object includes: determining the visual axis center based on a built-in positioning system and/or a corneal topography via an excimer laser device.

In some embodiments, determining the visual axis center based on the built-in positioning system and/or the corneal topography via the excimer laser device includes: determining a cutting diameter and a cutting depth via a phototherapeutic keratectomy (PTK) mode; importing a pupil offset in the corneal topography; and determining the visual axis center.

In some embodiments, the cutting diameter and the cutting depth may be set based on the requirements. For example, the cutting depth is related to an implant property, biomechanical safety, and an optical effect of the lens implanted in the cornea.

In some embodiments, the cutting diameter may be 0.5 mm.

In some embodiments of the present disclosure, finer corneal cutting can be achieved and damage to the cornea can be reduced by setting the cutting diameter to 0.5 mm.

In some embodiments, the cutting diameter may also be 0.3 mm, 0.4 mm, or the like.

In some embodiments, the cutting depth may be in a range of 30-40 μm.

In some embodiments, the cutting depth may be 32 μm, 34 μm, 36 μm, 38 μm, 40 μm, or the like.

In some embodiments, the cutting depth may be in a range of 30-35 μm, in a range of 35-40 μm, or the like.

In some embodiments, the cutting depth may be in a range of 30-32 μm, in a range of 32-34 μm, in a range of 34-36 μm, in a range of 36-38 μm, in a range of 38-40 μm, or the like.

In some embodiments of the present disclosure, the cutting depth is set to a range of 30-40 μm, thereby ensuring that the depth of the corneal implant cavity is appropriate, and improving the stability of the lens.

The pupil offset refers to an offset distance between a pupil center of the target object and an ideal optical center. The ideal optical center may be a geometric center of the cornea.

In some embodiments of the present disclosure, visual axis positioning is performed by using the excimer laser device, the built-in positioning system, and the corneal topography, thereby improving positioning accuracy to make the lens more accurately aligned to the visual axis, significantly reducing problems such as glare, a halo and a high-order aberration caused by eccentricity; and improving postoperative visual clarity and patient satisfaction.

In some embodiments, the method for implanting the corneal inlay further includes: dyeing and marking the visual axis center of the target object.

In some embodiments of the present disclosure, dyeing and marking the visual axis center is convenient for the user to identify the position of the visual axis center, thereby improving convenience and accuracy of the surgery.

In 120, the corneal implant cavity for the target object is produced.

The corneal implant cavity refers to a luminal structure that is created when the cornea is implanted. In some embodiments, the corneal implant cavity may include a corneal tunnel, a pouch, or the like.

In some embodiments, producing the corneal implant cavity for the target object includes: producing the corneal implant cavity for the target object based on a preset condition via a laser device. The preset condition may be set based on factors such as a corneal curvature, a thickness, an expected correction amount and a type of the lens. The laser device refers to a device that cuts a corneal stroma layer by laser technology. For example, the laser device may include a femtosecond laser device, etc.

In some embodiments, producing the corneal implant cavity for the target object includes: cutting within the corneal stroma layer of the target object based on the cutting diameter and the cutting depth; and separating corneal lamellae. More descriptions regarding the cutting diameter and the cutting depth may be found in operation 110 and related descriptions thereof.

In some embodiments, the corneal implant cavity is acquired by cutting within the corneal stroma layer of the target object to the cutting diameter and the cutting depth.

In some embodiments, the corneal lamellae may be separated via a separator. The separator refers to a device that separates the different layers of the cornea, such as the anterior elastic layer, a stroma layer, or the endothelial layer. In some embodiments, excess corneal stroma during cutting may be removed by the separator.

In some embodiments, the separator includes a lens separator. Excess corneal stroma during the cutting process may be removed by the lens separator.

In some embodiments of the present disclosure, using the lens separator is more in line with an anatomical structure of the cornea, thereby reducing mechanical damage to the surrounding tissues and reducing the risk of postoperative complications. At the same time, the lens separator has a higher precision, which can separate the different layers of the cornea more efficiently and ensure smooth implantation of the lens.

In some embodiments of the present disclosure, precise cutting in the corneal stroma layer by the laser device can create a cavity suitable for lens implantation and improve a success rate of the surgery. The removal of corneal tissue during surgery can be ensured by the separator, thereby improving the safety and efficacy of the surgery.

In some embodiments, a cutting entrance to the corneal stroma layer is located on a temporal side of the target object, and a width of the cutting entrance is greater than or equal to a diameter of the lens.

The cutting entrance refers to an incision to a corneal surface. The width of the cutting entrance refers to a width of the incision to the corneal surface.

In some embodiments, a size of the corneal implant cavity is slightly larger than a size of the lens (e.g., a width of the corneal implant cavity is 1 mm larger than the diameter of the lens), thereby ensuring that the corneal inlay fits adequately into the surrounding tissues of the cornea and avoiding displacement or rejection.

In some embodiments of the present disclosure, damage to the cornea can be minimized and lens implantation can be facilitated by setting the cutting entrance on the temporal side.

In 130, an intraocular pressure of the target object is adjusted.

Figure 2:
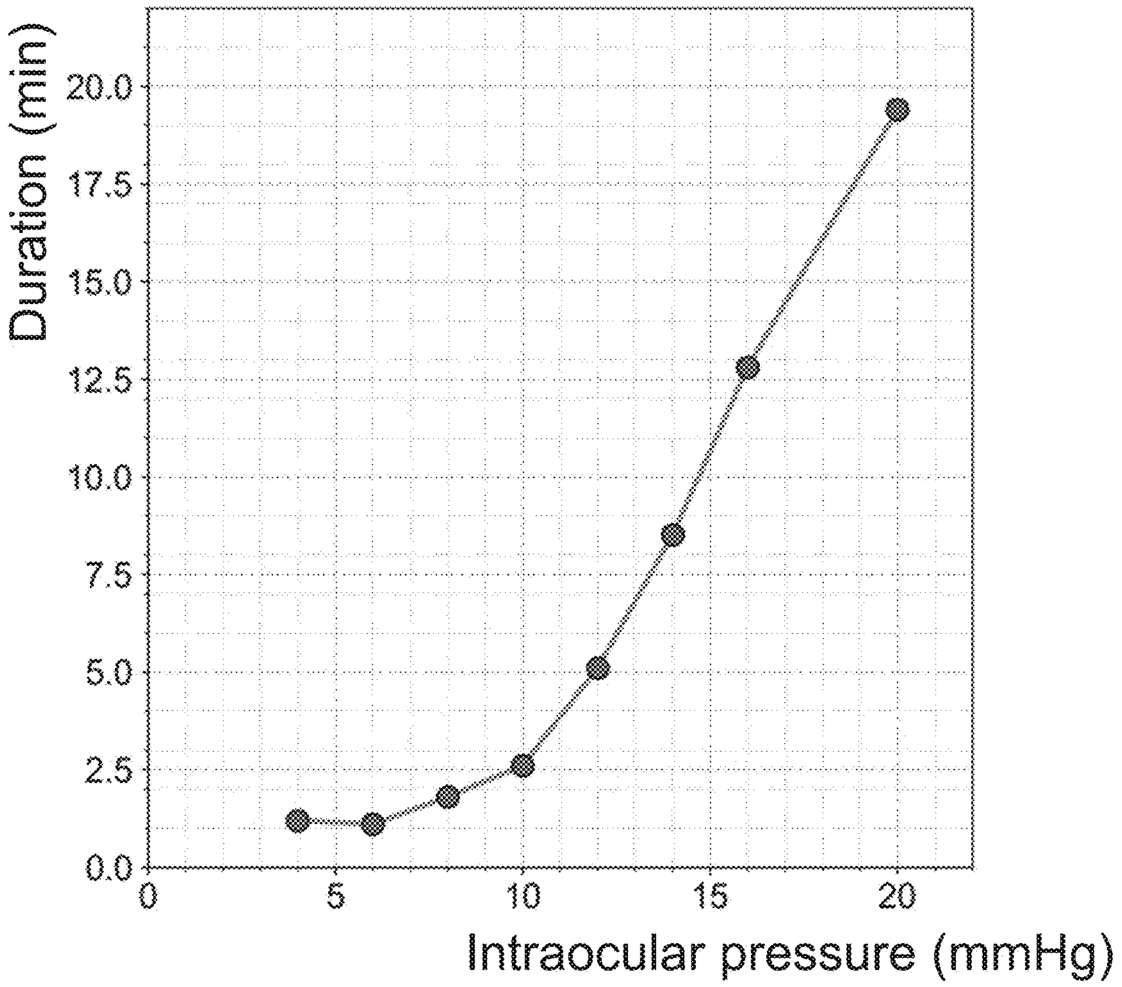
FIG. 2 is a schematic diagram illustrating changes of a duration with an intraocular pressure in a surgery of implanting a corneal inlay according to the present disclosure.

FIG. 2 is a schematic diagram illustrating changes of a duration with an intraocular pressure in a surgery for implanting a corneal inlay according to the present disclosure. In some embodiments, the duration during a surgery procedure is directly proportional to the intraocular pressure of the surgical procedure. The higher the intraocular pressure, the longer the duration of the surgical procedure. Exemplarily, the relationship between the intraocular pressure and the duration of the surgical procedure is shown in FIG. 2.

In some embodiments, adjusting the intraocular pressure of the target object includes: making an incision around a cornea of the target object to release aqueous humor and adjust the intraocular pressure to make the intraocular pressure in a range of 5-10 mmHg.

In some embodiments, the intraocular pressure is in a range of 5-6 mmHg, 7-8 mmHg, 9-10 mmHg, etc.

In some embodiments, the intraocular pressure is 6 mmHg.

In some embodiments, the intraocular pressure is 5 mmHg, 7 mmHg, 8 mmHg, 9 mmHg, 10 mmHg, etc.

In some embodiments, the incision may be created by, for example, a corneal incision knife or a micro scissor device.

In some embodiments, the incision is created using a 15° puncture knife.

In some embodiments of the present disclosure, the incision is created using the 15° puncture knife, so that the process for adjusting the intraocular pressure can be precisely controlled to ensure accuracy and safety of the incision, thereby improving efficiency and stability of adjusting the intraocular pressure.

In some embodiments of the present disclosure, corneal tension can be reduced by lowering the intraocular pressure, so that the stromal tunnel is in a state of low tension, and the lens is more easily implanted and remains stable; an operation time is greatly shortened to reduce corneal dilatation or an incision tension-related complication; and the repeated pulling of corneal tissue during surgery is reduced to prevent deformation or positional deviation of the lens due to excessive resistance.

In 140, the lens is implanted into the corneal implant cavity of the target object to align the lens with the visual axis center of the target object.

In some embodiments, a thickness and an implantation depth of the lenses may be set based on the requirements. Lenses with different thicknesses and implantation depths are implanted to achieve different corrective effects. A refractive power of the lens needs to be higher than an expected correction to avoid under correction.

In some embodiments, implanting the lens into the corneal implant cavity of the target object to align the lens with the visual axis center of the target object includes: implanting the lens into the corneal implant cavity; and adjusting the lens to align the lens with the visual axis center.

In some embodiments of the present disclosure, the lens is adjusted to align the lens with the visual axis center, so that the optimal position of the lens can be ensured to improve vision correction.

Figure 3:
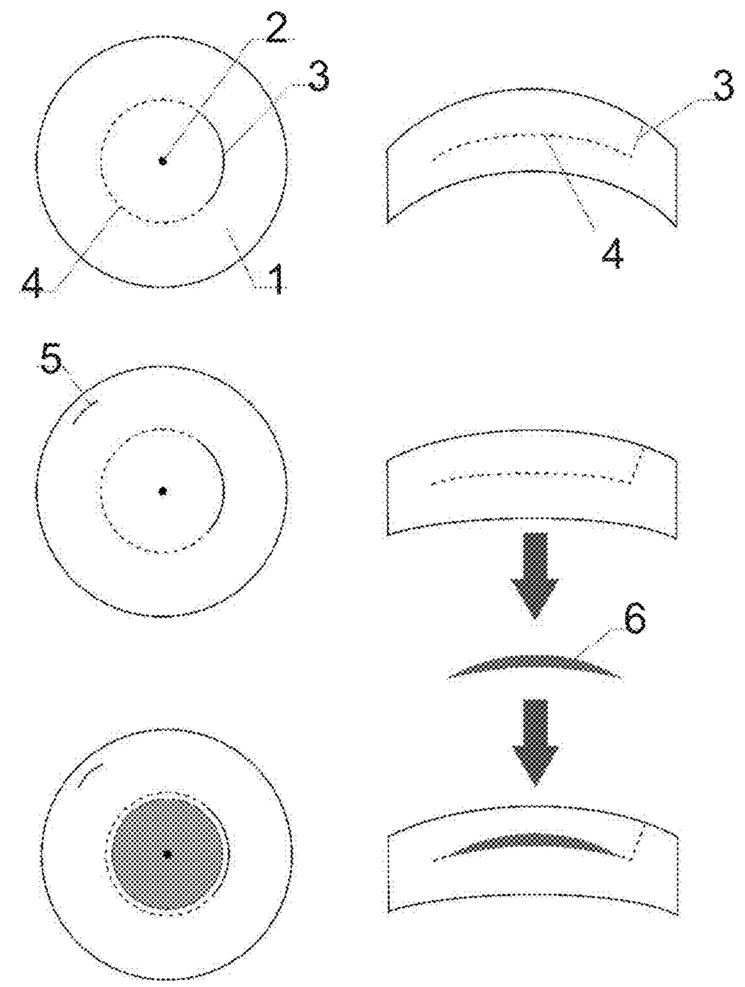
FIG. 3 is a schematic diagram illustrating a process for implanting a corneal inlay according to some embodiments of the present disclosure.

FIG. 3 is a schematic diagram illustrating a process for implanting a corneal inlay according to some embodiments of the present disclosure. Merely by way of example, as shown in FIG. 3, a method for implanting a corneal inlay includes: dyeing and marking a visual axis center 2 on a cornea 1; cutting within a corneal stroma layer using a femtosecond laser device to obtain a cutting entrance 3 and a corneal implant cavity 4; making an incision 5 on an outer side of the cornea; releasing aqueous humor from the incision 5; and implanting a lens 6 into the corneal implant cavity 4 through the cutting entrance 3 via an implantation instrument.

Since the corneal inlay is a thin lens which is easily curled, the corneal inlay needs to be unfolded before implantation. Therefore, a specialized implantation instrument is necessary.

In some embodiments, implanting the lens into the corneal implant cavity of the target object is performed via an implantation instrument. In some embodiments, as shown in FIG. 4-FIG. 8, the implantation instrument includes: an outer sheath 71; an inner push rod 72, wherein the inner push rod 72 is disposed in the outer sheath 71, a relative position between the inner push rod 72 and the outer sheath 71 is capable of changing; an unfolding and pushing structure 73 disposed at a first end of the inner push rod 72, wherein the unfolding and pushing structure 73 is in a contraction state when the unfolding and pushing structure 73 retracts into the outer sheath 71, the unfolding and pushing structure 73 is in an unfolding state when the unfolding and pushing structure 73 extends out of the outer sheath 71; an extending length of the unfolding and pushing structure 73 extending out of the outer sheath 71 is different from an unfolding width of the unfolding and pushing structure 73. Unfolding rods 731 are disposed on both sides of the unfolding and pushing structure 73, wherein the unfolding and pushing structure 73 in the unfolding state performs an unfolding effect on the lens, and frictional forces exerted on the lens by the unfolding rods 731 perform a pushing effect. In some embodiments, the unfolding and pushing structure 73 includes a central rod 732, wherein a fork portion is disposed on an end of the central rod 732, the lens is disposed in a center of the fork portion, the fork portion of the central rod 732 performs the pushing effect, and the unfolding and pushing structure 73 in the unfolding state performs the unfolding effect on the lens. In some embodiments, an unfolding width of the unfolding and pushing structure 73 varies with an extension length of the unfolding and pushing structure 73. In some embodiments, the unfolding rods 731 and a central axis of the central rod 732 in the unfolding state is located in the same plane, and frictional forces exerted on the lens by both the unfolding rods 731 and the central rod 732 perform the pushing effect. It should be noted that although there is the central rod 732 in FIG. 4-FIG. 8, when the pushing effect is performed through the frictional forces, the unfolding and pushing structure 73 may be provided with only two unfolding rods 731.

Figure 8:
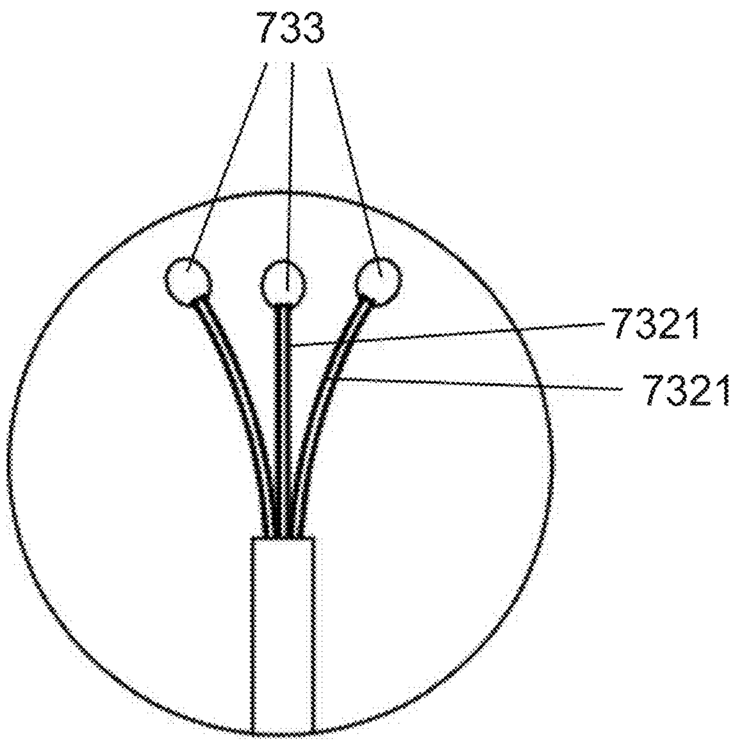
FIG. 8 is a schematic diagram of a front view of a partially enlarged structure of an end of an exemplary implantation instrument according to some embodiments of the present disclosure, wherein a small ball structure is provided on the end of the middle rod.

In some embodiments, as shown in FIG. 8, when the central rod 732 does not have the fork portion, the inner push rod 72 enters the cornea along with the outer sheath 71 in the contraction state and contacts a curled lens in the corneal lamellae. A position of the outer sheath 71 is kept and the unfolding and pushing structure 73 is pushed out of the outer sheath 71 to position the unfolding rods 731 of the unfolding and pushing structure 73 above the lens. During a pushing process of the unfolding rods 731, a distance between the two unfolding rods 731 increases to unfold the curled lens, and the unfolding rods 731 maintain the unfolding effect on the lens. The ends of the unfolding rods 731 and the central rod 732 are in close contact with the lens, creating a static frictional force that pushes the lens.

In some embodiments, the unfolding and pushing structure 73 includes the central rod 732 when the frictional forces exerted on the lens by the unfolding rods 731 perform the pushing effect, and in the unfolding state, the end of the central rod 732 is lower than ends of the unfolding rods 731. The above structure ensures a triangular pushing structure 75 and reduces an overall length of the triangular pushing structure 75. The end of the central rod 732 and the ends of the unfolding rods 731 refer to ends away from the outer sheath 71. In the unfolding state, a distance from the end of the central rod 732 to the end of the outer sheath 71 is shorter than a distance from the ends of the unfolding rods 731 to the end of the outer sheath 71.

Figure 6:
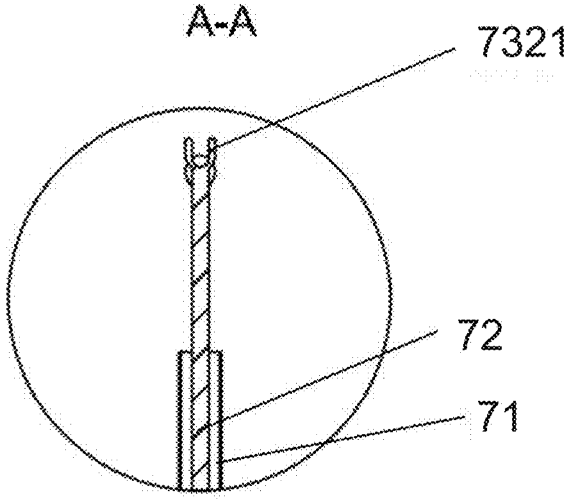
FIG. 6 is a schematic diagram of a partially enlarged longitudinal section structure of an end of an exemplary implantation instrument under a side view according to some embodiments of the present disclosure, wherein an unfolding and pushing structure is in an unfolding state, and an end of a central rod is provided with a fork portion.
Figure 7:
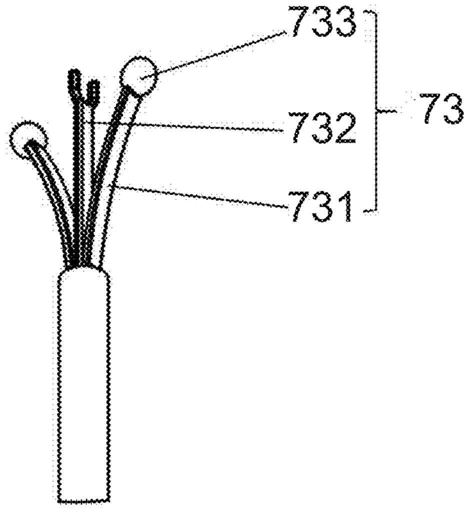
FIG. 7 is a schematic diagram of a partially enlarged structure of an end of an exemplary implantation instrument under a main view according to some embodiments of the present disclosure, wherein an unfolding and pushing structure is in an unfolding state, and an end of a central rod is provided with a fork portion.

In some embodiments, as shown in FIG. 6-FIG. 7, when the central rod 732 has the fork portion, the inner push rod 72 enters the cornea along with the outer sheath 71 in the contraction state and contacts the curled lens in the corneal lamellae. A position of the outer sheath 71 is kept, and the unfolding and pushing structure 73 is slightly pushed out of the outer sheath 71. When the central rod 732 extends out of the outer sheath 71 before the unfolding rods 731, fork prongs 7321 in an upper position and a lower position of fork portion are disposed on the two sides of the lens to deform the lens, so that the unfolding rods 731 are able to disposed inside the curled lens. The curled lens is unfolded when the unfolding and pushing structure 73 is pushed out, the lens is sent to a correct position in an unfolding state using a pushing force of the fork prongs 7321 and the unfolding effect of the unfolding rods 731, thereby ensuring smooth engagement of the fork prongs 7321, making the entire process more seamless. When the central rod 732 extends out of the outer sheath 71 after the unfolding rods 731, the unfolding rods 731 are first inserted into the curled lens and are gradually extended to fully unfold the curled lens. After unfolding, the fork prongs 7321 are also extended, and the implantation instrument is retracted so that edges of the fork portion contact edges of the lens. The fork portion and the lens are adjusted to position the lens within the fork portion, and the fork portion provides the pushing effect. The above manner reduces a significant deformation risk of the lens by the fork prongs 7321 and better coordinates with the unfolding rods 731 to perform the pushing effect and unfolding effect.

Figure 4:
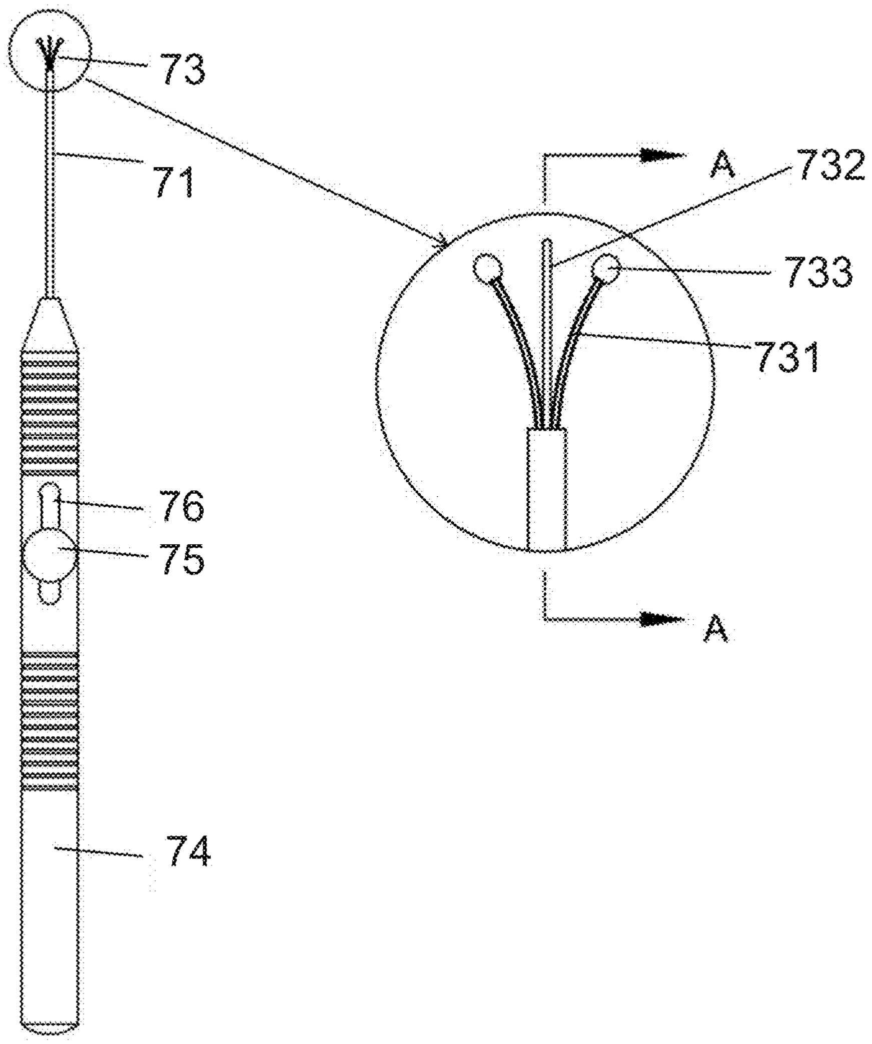
FIG. 4 is a schematic diagram of a front view structure of an exemplary implantation instrument and a partially enlarged structure of an end thereof according to some embodiments of the present disclosure, wherein an unfolding and pushing structure is in an unfolding state, and an end of a central rod is provided with a fork portion.
Figure 5:
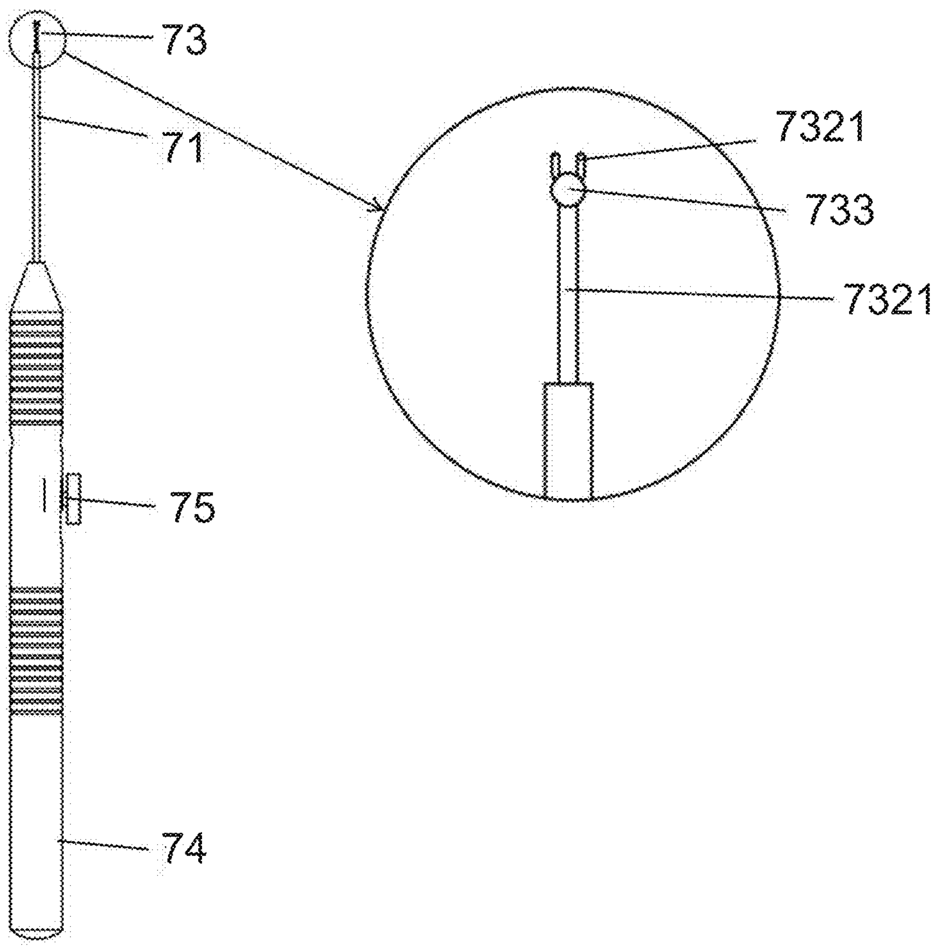
FIG. 5 is a schematic diagram of a side view structure of an exemplary implantation instrument and a partially enlarged structure of an end thereof according to some embodiments of the present disclosure, wherein an unfolding and pushing structure is in an unfolding state, and an end of a central rod is provided with a fork portion.

In some embodiments, as shown in FIG. 4 and FIG. 5, an operating handle is disposed on a rear end of the outer sheath 71, the operating handle is provided with a pushing structure connected to the inner push rod 72, a contraction position when the unfolding and pushing structure 73 is in the contraction state and an unfolding position when the unfolding and pushing structure 73 is in the unfolding state are disposed on the operating handle; the unfolding and pushing structure is in the contraction state when the pushing structure is in the contraction position, and the unfolding and pushing structure is in the unfolding state when the pushing structure is in the unfolding position. The operating handle 74 is also provided with a sliding groove 76 of the pushing structure 75, thereby allowing the pushing structure 75 to move between the contraction position and the unfolding position. The pushing structure 75 may stop at any position between the contraction position and the unfolding position, thereby enabling adjustment of an unfolding degree of the unfolding rods 731 based on requirements. The pushing structure 75 is in close contact with the sliding groove 76, and the pushing structure 75 does not move without an external force, so that the pushing structure 75 stops stably at any position and the unfolding rods 731 exist in any required unfolding state. To ensure position stability, a locking mechanism may be disposed on the pushing structure 75. The locking mechanism may be any structure that secures the pushing structure 75 to the operating handle 74, e.g., a locking nut or locking fork prongs.

In some embodiments, as shown in FIG. 7 and FIG. 8, each of ends of the unfolding rods 731 is provided with a spherical structure 733, and when the frictional forces between the unfolding rods 731 and the lens perform the pushing effect, the end of the central rod 732 is disposed with a spherical structure 733, the spherical structure 733 is a rough sphere. The spherical structure 733 prevents tissue damage during operation. A rough surface of the spherical structure 733 ensures effective static frictional force when in contact with the lens, thereby providing a reliable pushing force.

In some embodiments, in the contraction state, a center of the spherical structure 733 and a center of the fork portion lie on the same line, and the spherical structure 733 extends into the fork. In the contraction state, a width of each of the unfolding rods 731 and a width of the central rod 732 are a sum of diameters of two spherical structures 733. The above structure ensures that the unfolding rods 731 and the central rod 732 are contracted within the outer sheath 71 in a smallest width, thereby reducing an outer diameter of the outer sheath 71, minimizing an incision size required for the outer sheath 71 to enter the cornea, and reducing harm to patients when implanting the corneal inlay.

In some embodiments, the unfolding rods 731 and the central rod 732 are both designed as plate-like rods with a thickness of 0.1 mm. The plate-like rods ensure an overall strength while preventing excessive thickness of the unfolding rods 731 and the central rod 732 in the contraction state, thereby allowing the unfolding rods 731 and the central rod 732 to be better contracted into the outer sheath 71.

In some embodiments, an unfolding distance between the two unfolding rods 731 in a fully unfolding state is 24 mm. In some embodiments, the unfolding distance may be any distance in a range of 20-30 mm. The central rod 732 is a straight rod with a length range of 20-25 mm.

In some embodiments, when the central rod 732 includes the fork portion, an outer distance between the two fork prongs 7321 is 0.75 mm, with a variation range of 0.2 mm.

An inner distance between the two fork prongs 7321 is 0.4 mm, with a variation range of 0.2 mm.

In some embodiments, a diameter of the spherical structure 733 is 0.6 mm, with a variation range of 0.2 mm.

In some embodiments, an overall length of the implantation instrument is 148 mm, with a variation range of 20 mm. A longitudinal axis of the operating handle 74 aligns with a longitudinal axis of the outer sheath 71, wherein a length of the operating handle 74 is 90 mm, with a variation range of 10 mm. The above ranges meet the requirements for unfolding and pushing the corneal inlay.

The method of implanting the corneal inlay according to some embodiments of the present disclosure can improve precision and stability of the surgery, and ensure that the lens is aligned with the visual axis center, thereby improving vision correction.

In some embodiments, the method for implanting the corneal inlay further includes a postoperative adjustment including: checking and confirming a position of the lens after a surgery via at least one of a slit lamp or an optical coherence tomography (OCT) examination; and in response to the position of the lens is skewed, adjusting the lens to align the lens with the visual axis center.

In some embodiments of the present disclosure, the postoperative adjustment can be made to ensure the accuracy of the position of the lens, thereby improving a long-term result of the surgery.

In some embodiments, the method for implanting the corneal inlay further includes removing and/or replacing the lens. In some embodiments, removing the lens includes: removing the lens by cooperating with the microscopic instrument. In some embodiments, replacing the lens includes: removing an original lens and adjusting the intraocular pressure of the target object; and implanting a new lens and adjusting a position of the new lens.

In some embodiments, replacing the lens includes: removing the original lens, making a new incision either through an incision in the original cornea or using the 15° puncture knife, releasing a small amount of aqueous humor, and re-implanting and repositioning the lens.

In some embodiments of the present disclosure, the flexibility and reversibility of the procedure can be improved and adapted to the needs of different patients by providing manners of removing and replacing the lens.

In some embodiments, the method for implanting the corneal inlay further includes: disinfecting a surgical operation region and/or a surrounding region of the surgical operation region. In some embodiments, disinfecting may be performed before, during, and/or after the surgery for implanting the corneal inlay.

Some embodiments of the present disclosure provide a method for facilitating implanting a corneal inlay, including performing an intraocular pressure adjustment before implanting the corneal inlay.

Some embodiments of the present disclosure provide a method for vision correction, including the method for implanting the corneal inlay as described in any one of the present disclosure.

In some embodiments, indications for correcting vision include presbyopia, hyperopia, corneal ectasia, or the like.

The basic concepts have been described above, and it is apparent to those skilled in the art that the foregoing detailed disclosure serves only as an example and does not constitute a limitation of the present disclosure. While not expressly stated herein, a person skilled in the art may make various modifications, improvements, and amendments to the present disclosure. Those types of modifications, improvements, and amendments are suggested in the present disclosure, so those types of modifications, improvements, and amendments remain within the spirit and scope of the exemplary embodiments of the present disclosure.

Also, the present disclosure uses specific words to describe embodiments of the present disclosure. such as "one embodiment", "an embodiment", and/or "some embodiment" means a feature, structure, or characteristic associated with at least one embodiment of the present disclosure. Accordingly, it should be emphasized and noted that two or more references in the present disclosure, at different locations, to "one embodiment" or "an embodiment" or "an alternative embodiment" in different places in the present disclosure do not necessarily refer to the same embodiment. In addition, certain features, structures, or characteristics in one or more embodiments of the present disclosure may be suitably combined.

Furthermore, the order of the processing elements and sequences described herein, the use of numerical letters, or the use of other names are not intended to limit the order of the processes and methods herein. While a number of embodiments of the invention that are currently considered useful are discussed in the foregoing disclosure by way of various examples, it should be understood that such details serve illustrative purposes only. For example, although the implementation of various components described above may be embodied in a hardware device, it may also be implemented as a software only solution, e.g., an installation on an existing server or mobile device.

Similarly, it should be noted that in order to simplify the presentation of the disclosure of the present disclosure, and thereby aid in the understanding of one or more embodiments of the invention, the foregoing descriptions of embodiments of the present disclosure sometimes group multiple features together in a single embodiment, accompanying drawings, or in a description thereof. description thereof. Rather, claimed subject matter may lie in less than all features of a single foregoing disclosed embodiment.

Some embodiments use numbers to describe the number of components, attributes, and it should be understood that such numbers used in the description of the embodiments are modified in some examples by the modifiers "about", "approximately", or "substantially".", or "generally" is used in some examples. Unless otherwise noted, the terms "proximately" or "approximately" indicates that a ±20% variation in the stated number is allowed. Correspondingly, in some embodiments, the numerical parameters used in the present disclosure are approximations, which can change depending on the desired characteristics of individual embodiments. In some embodiments, the numerical parameters should take into account the specified number of valid digits and employ general place-keeping. While the numerical domains and parameters used to confirm the breadth of their ranges in some embodiments of the present disclosure are approximations, in specific embodiments such values are set to be as precise as possible within a feasible range.

Finally, it should be understood that the embodiments described in the present disclosure are only used to illustrate the principles of the embodiments of the present disclosure. Other deformations may also fall within the scope of the present disclosure. As such, alternative configurations of embodiments of the present disclosure may be considered to be consistent with the teachings of the present disclosure as an example, not as a limitation. Correspondingly, the embodiments of the present disclosure are not limited to the embodiments expressly presented and described herein.

What is claimed is:

1. A method for implanting a corneal inlay based on visual axis positioning and intraocular pressure adjustment, comprising:

determining a cutting diameter and a cutting depth via a phototherapeutic keratectomy (PTK) mode of an excimer laser device;

importing a pupil offset in a corneal topography, via the excimer laser device, to determine a visual axis center, wherein the pupil offset includes an offset distance between a pupil center of a target object and an ideal optical center, and the ideal optical center includes a geometric center of a cornea;

cutting within a corneal stroma layer of the target object based on the cutting diameter and the cutting depth; and separating corneal lamellae and obtaining a corneal implant cavity;

making an incision around the cornea of the target object to release aqueous humor and adjust an intraocular pressure to make the intraocular pressure in a range of 5-10 mmHg; and implanting a lens into the corneal implant cavity of the target object to align the lens with the visual axis center of the target object.

2. The method of claim 1, wherein the method further comprises: dyeing and marking the visual axis center of the target object.

3. The method of claim 1, wherein the cutting diameter is 0.5 mm.

4. The method of claim 1, wherein the cutting depth is in a range of 30-40 μm.

5. The method of claim 1, wherein a cutting entrance to the corneal stroma layer is located on a temporal side of the target object, and a width of the cutting entrance is greater than or equal to a diameter of the lens, wherein the temporal side of the target object refers to a side of the target object close to a temple.

6. The method of claim 1, wherein the intraocular pressure is 6 mmHg.

7. The method of claim 6, wherein implanting the lens into the corneal implant cavity of the target object is performed via an implantation instrument, wherein the implantation instrument includes:

an outer sheath;

an inner push rod disposed in the outer sheath, wherein a relative position between the inner push rod and the outer sheath is capable of changing;

an unfolding and pushing structure disposed at a first end of the inner push rod, wherein the unfolding and pushing structure is in a contraction state when the unfolding and pushing structure retracts into the outer sheath, the unfolding and pushing structure is in an unfolding state when the unfolding and pushing structure extends out of the outer sheath, wherein an unfolding width of the unfolding and pushing structure varies with an extension length of the unfolding and pushing structure from the outer sheath;

unfolding rods are disposed on both sides of the unfolding and pushing structure, wherein the unfolding and pushing structure in the unfolding state performs an unfolding effect on the lens, and frictional forces exerted on the lens by the unfolding rods perform a pushing effect; or the unfolding and pushing structure includes a central rod, wherein a fork portion is disposed on an end of the central rod, the lens is disposed in a center of the fork portion, the fork portion of the central rod performs the pushing effect, and the unfolding and pushing structure in the unfolding state performs the unfolding effect on the lens.

8. The method of claim 7, wherein the unfolding and pushing structure includes the central rod when the unfolding and pushing structure performs the pushing effect via the frictional forces, and in the unfolding state, the end of the central rod is lower than ends of the unfolding rods.

9. The method of claim 8, wherein an operating handle is disposed on a rear end of the outer sheath, the operating handle is provided with a pushing structure connected to the inner push rod, a contraction position when the unfolding and pushing structure is in the contraction state and an unfolding position when the unfolding and pushing structure is in the unfolding state are disposed on the operating handle; the unfolding and pushing structure is in the contraction state when the pushing structure is in the contraction position, and the unfolding and pushing structure is in the unfolding state when the pushing structure is in the unfolding position.

10. The method of claim 7, wherein each of ends of the unfolding rods is provided with a spherical structure, and when the frictional forces between the unfolding rods and the lens perform the pushing effect, the end of the central rod is disposed with a spherical structure, the spherical structure is a rough sphere.

11. The method of claim 1, wherein the method further comprises a postoperative adjustment including:

checking and confirming a position of the lens after a surgery via at least one of a slit lamp or an optical coherence tomography (OCT) examination; and in response to the position of the lens is skewed, adjusting the lens to align the lens with the visual axis center.

12. The method of claim 1, wherein the method further comprises removing and/or replacing the lens, wherein:

removing the lens includes:

removing the lens by cooperating with a microscopic instrument; and replacing the lens includes:

removing an original lens and adjusting the intraocular pressure of the target object; and implanting a new lens and adjusting a position of the new lens.

13. The method of claim 1, wherein the method further comprises: disinfecting a surgical operation region and/or a surrounding region of the surgical operation region.

14. A method for facilitating implanting a corneal inlay, comprising:

cutting within a corneal stroma layer of a target object based on a cutting diameter and a cutting depth; and separating corneal lamellae and obtaining a corneal implant cavity;

before implanting a corneal inlay, making an incision around a cornea of the target object to release aqueous humor and adjust an intraocular pressure to make the intraocular pressure in a range of 5-10 mmHg; and implanting a lens into the corneal implant cavity of the target object to align the lens with the visual axis center of the target object.

15. A method for vision correction by implanting a corneal inlay based on visual axis positioning and intraocular pressure adjustment, the method comprising:

determining a cutting diameter and a cutting depth via a phototherapeutic keratectomy (PTK) mode of an excimer laser device;

importing a pupil offset in a corneal topography, via the excimer laser device, to determine a visual axis center, wherein the pupil offset includes an offset distance between a pupil center of a target object and an ideal optical center, and the ideal optical center includes a geometric center of a cornea;

cutting within a corneal stroma layer of the target object based on the cutting diameter and the cutting depth; and separating corneal lamellae and obtaining a corneal implant cavity;

making an incision around a cornea of the target object to release aqueous humor and adjust an intraocular pressure to make the intraocular pressure in a range of 5-10 mmHg; and implanting a lens into the corneal implant cavity of the target object to align the lens with the visual axis center of the target object.

16. The method of claim 15, wherein indications for vision correction include presbyopia, hyperopia, and corneal ectasia.

* * * * *